US008273395B2

(12) United States Patent
Colliver et al.

(10) Patent No.: US 8,273,395 B2
(45) Date of Patent: Sep. 25, 2012

(54) PROCESS FOR MANUFACTURING TEA PRODUCTS

(75) Inventors: Steven Peter Colliver, Sharnbrook (GB); David George Sharp, Sharnbrook (GB); Ian Smith, Sharnbrook (GB)

(73) Assignee: Conopco, Inc., Englewood Cliffs, NJ (US)

( * ) Notice: Subject to any disclaimer, the term of this patent is extended or adjusted under 35 U.S.C. 154(b) by 339 days.

(21) Appl. No.: 12/290,859

(22) Filed: Nov. 4, 2008

(65) Prior Publication Data
US 2009/0117250 A1 May 7, 2009

(30) Foreign Application Priority Data

| Nov. 5, 2007 | (EP) | 07119984 |
|---|---|---|
| Nov. 5, 2007 | (EP) | 07119988 |
| Nov. 12, 2007 | (EP) | 07120447 |
| Nov. 12, 2007 | (EP) | 07120448 |
| Dec. 19, 2007 | (EP) | 07123586 |
| Feb. 7, 2008 | (EP) | 08151155 |
| Oct. 2, 2008 | (EP) | 08165775 |
| Oct. 2, 2008 | (EP) | 08165776 |

(51) Int. Cl.
*A23F 3/16* (2006.01)
(52) U.S. Cl. ......... 426/435; 426/597; 426/489; 426/443
(58) Field of Classification Search .................. 426/597, 426/489, 443
See application file for complete search history.

(56) References Cited

U.S. PATENT DOCUMENTS

| 3,821,440 | A | 6/1974 | Reeve | 426/312 |
|---|---|---|---|---|
| 4,051,264 | A | 9/1977 | Sanderson et al. | 426/52 |
| 4,880,656 | A | 11/1989 | Schütz et al. | 426/386 |
| 7,074,451 | B2 | 7/2006 | Succar et al. | 426/49 |
| 7,108,877 | B2 | 9/2006 | Blair et al. | 426/49 |
| 7,232,585 | B2 | 6/2007 | Quan et al. | 426/597 |
| 2004/0001862 | A1 | 1/2004 | Xiu | 424/195.17 |
| 2004/0180077 | A1 | 9/2004 | Riker et al. | 424/439 |
| 2005/0008753 | A1 | 1/2005 | Honda et al. | 426/590 |
| 2005/0181079 | A1 | 8/2005 | Koganov | 424/729 |
| 2006/0210653 | A1 | 9/2006 | Gardiner et al. | 424/729 |
| 2006/0257547 | A1 | 11/2006 | Honda et al. | 426/655 |
| 2007/0071870 | A1 | 3/2007 | You | 426/597 |
| 2007/0231445 | A1 | 10/2007 | Gehrig et al. | 426/597 |

FOREIGN PATENT DOCUMENTS

| CN | 1 039 525 | 2/1990 |
|---|---|---|
| CN | 1 219 359 | 6/1999 |
| CN | 1 266 625 | 9/2000 |
| CN | 1 356 054 | 7/2002 |
| CN | 1 396 249 | 2/2003 |
| CN | 1 718 030 | 1/2006 |
| CN | 101 002 587 | 7/2007 |
| CN | 101 044 878 | 10/2007 |
| CN | 101 385 491 | 3/2009 |
| CN | 101 491 281 | 7/2009 |
| EP | 0 167 399 | 1/1986 |
| EP | 1 013 261 | 6/2000 |
| EP | 1 062 941 | 12/2000 |
| GB | 593 260 | 10/1947 |
| GB | 893 551 | 4/1963 |
| GB | 968 423 | 9/1964 |
| GB | 1 284 721 | 8/1972 |
| GB | 1 329 612 | 9/1973 |
| GB | 11 310 | 5/2011 |
| IN | 195 073 | 2/2001 |
| JP | 02 184626 | 7/1990 |
| JP | 05/211838 | 8/1993 |
| JP | 07/203849 | 8/1995 |
| JP | 09 275 903 | 10/1997 |
| JP | 10/165095 | 6/1998 |
| JP | 10/304822 | 11/1998 |
| JP | 11/009188 | 1/1999 |
| JP | 11 056 243 | 3/1999 |
| JP | 11/346654 | 12/1999 |
| JP | 2000/125824 | 5/2000 |
| JP | 2003/111558 | 4/2003 |
| JP | 2003/125705 | 5/2003 |
| JP | 2003/164261 | 6/2003 |
| JP | 2004/041237 | 2/2004 |
| JP | 2004/089146 | 3/2004 |
| JP | 2006/136270 | 6/2006 |
| JP | 2007/082526 | 4/2007 |
| KR | 1994-0000775 | 8/1992 |
| KR | 10 2009 0009042 | 1/2009 |
| RU | 326 797 | 12/1972 |
| RU | 929 041 | 5/1982 |
| RU | 1 153 873 | 5/1985 |
| WO | 97/20686 | 6/1997 |
| WO | 98/23164 | 6/1998 |
| WO | 99/40799 | 8/1999 |
| WO | 00/47056 | 8/2000 |
| WO | 01/82713 | 11/2001 |
| WO | 02/069727 | 9/2002 |

(Continued)

OTHER PUBLICATIONS

PCT International Search Report in a PCT application PCT/EP2008/064713.
European Search Report in an EP application EP 07 11 9988.
European Search Report in an EP application EP 07 11 9984.
PCT International Search Report in a PCT application PCT/EP2008/064714.
European Search Report in an EP application EP 08 15 1155.
PCT International Search Report in a PCT application PCT/EP2008/064716.
Derwent Abstract of WO2008/001848 published Jan. 3, 2008.
Abstract of CN 1 058 135—published Jan. 29, 1992 with full text translation.
Abstract of CN 1 059 078—published Mar. 4, 1992.
Abstract of CN 1 640 282—published Jul. 20, 2005.
Abstract of KR 940004838—published Jun. 2, 1994.
Japanese Abstract 02-203746—published Aug. 13, 1990.
Japanese Abstract 05-292883—published Nov. 9, 1993.
Japanese Abstract 10-099021—published Apr. 21, 1998.
Japanese Abstract 10 101624—published Apr. 21, 1998.
Japanese Abstract 1 1-056243—published Feb. 2, 1999.

(Continued)

*Primary Examiner* — Anthony Weier
(74) *Attorney, Agent, or Firm* — Ellen Plotkin

(57) ABSTRACT

Shown is a process having the steps of: providing fresh tea material rich in stem; and expressing juice from the fresh tea material thereby to produce stem residue and tea juice having a mixture of tea compounds.

8 Claims, No Drawings

FOREIGN PATENT DOCUMENTS

| | | |
|---|---|---|
| WO | 03/022066 | 3/2003 |
| WO | 03/101215 | 12/2003 |
| WO | 2004/002235 | 1/2004 |
| WO | 2004/008869 | 1/2004 |
| WO | 2005/072532 | 8/2005 |
| WO | 2006/012238 | 2/2006 |
| WO | 2006/021317 | 3/2006 |
| WO | 2006/037503 | 4/2006 |
| WO | 2006/037504 | 4/2006 |
| WO | 2006/037511 | 4/2006 |
| WO | 2007/079900 | 7/2007 |
| WO | 2008/001848 | 1/2008 |
| WO | 2008/012280 | 1/2008 |
| WO | 2008/040627 | 4/2008 |
| WO | 2008/065007 | 6/2008 |
| WO | 2008/138706 | 11/2008 |

OTHER PUBLICATIONS

Japanese Abstract 2002-272369—published Sep. 24, 2002.
Japanese Abstract 2003-061581—published Mar. 4, 2003.
Japanese Abstract 2003-225054—published Aug. 12, 2003.
Japanese Abstract 2006-131512 published May 25, 2006.
Japanese Abstract 2006-206483 published Aug. 10, 2006.
Li et al., "*Current Research and Developments in the Processing of Green Tea Fresh Juice*" China Tea Processing, 2005, (2), pp. 23-24 and 29.
Sinija et al., "*Process technology for production of soluble tea powder*", Journal of Food Engineering, 82 (2007), pp. 276-283.
Nagao et al. "*Tea Catechins Suppress Accumulation of Body Fat in Humans*", J. Oleo Science, 50, (2001), pp. 717-728.
Peters et al., "*Does Tea Affect Cardiovascular Disease? A Meta-Analysis*", American Journal of Epidemiology, (2001), vol. 154, No. 6, pp. 495-503.
www.pref.kyoto.ip/chaken/ekisu.htrnl, "*The development of the tea extract powder*", at least before Oct. 2007.
Zhang et al., "*Reverse Osmosis Transport and Module analysis for Green Tea Juice Concentration*", Journal of Food Process Engineering, 1993, 16 (1), pp. 1-20).
Willson et al., "Tea Cultivation to consumption", 1$^{st}$ Edition, 1992, Chapter 13 (pp. 412-457), Chapter 14 (pp. 459-511); Chapter 16 (pp. 535-554), Chapter 17 (pp. 555-601).
"Determination of substances characteristic of green and black tea", International Standard, ISO 14502-1, First Edition, Mar. 1, 2005.
Wenli et al., "*Quality comparison of Fresh Green Tea Juice and green tea liquor*", Journal of Tea. (2003), 29(4) 215-216 (English Abstract attached).
Wenli et al., "*Research on the quality and processing technique of the fresh green tea iuice*".
Co-pending Application: Applicant: Colliver et al., U.S. Appl. No. 12/290,861, filed Nov. 4, 2008.
Co-pending Application: Applicant: Colliver et al., U.S. Appl. No. 12/290,860, filed Nov. 4, 2008.
Co-pending Application: Applicant Colliver et al., U.S. Appl. No. 12/290,858, filed Nov. 4, 2008.
Co-pending Application: Applicant Colliver et al., U.S. Appl. No. 12/290,857, filed: Nov. 4, 2008.
PCT International Search Report in a PCT application PCT/EP2009/051271.
PCT International Search Report in a PCT application PCT/EP2008/064720.
Co-pending Application: Applicant: Colliver et al., U.S. Appl. No. 12/322,410, filed Feb. 2, 2009.
PCT International Search Report in a PCT application PCT/EP2008/064717.
Sawai, et al., Content of γ-Aminobutync Acid in the Sterns of Anaerobically Treated Tea Shoots, Nat'l Research Institute of Vegetables, Ornamental Plants and Tea, Journal of the Food Science Technology Society of Japan, vol. 46, No. 4, pp. 274-277, 1999 (with Translation).
Iwaasa, Cultivation and Utilisation/Processing of Tea, K. K, Yokendo, K K. Seikosha, Aug. 29, 1994, pp. 370-371 (with Translation).
PCT international Search Report in a PCT application PCT/EP2009/062670.
PCT International search Report in a PCT application PCT/EP2009/062671.
European Search Report in an EP application EP 08 17 2695.
European Search Report in an EP application EP 08 17 2696.
Co-pending Application: Applicant: Colliver et al., U.S. Appl. No. 12/322,410, filed Feb. 29, 2009.
Co-pending Application: Applicant: Colliver et el., U.S. Appl. No.12/569,923, filed Sep. 30, 2009.
Co-pending Application: Applicant Colliver et al., U.S. Appl. No. 12/569,924, filed Sep. 30, 2009.

PROCESS FOR MANUFACTURING TEA PRODUCTS

TECHNICAL FIELD OF THE INVENTION

The present invention relates to a process for manufacturing products from tea. In particular the present invention relates to a process whereby juice is expressed from tea stem. The invention also relates to the juice expressed from stem.

BACKGROUND TO THE INVENTION

Tea is a beverage traditionally made by infusing the dry leaves of the plant *Camellia sinensis* in boiling water. Tea is (with the exception of water) probably the world's most popular beverage and, in some parts of the world, has traditionally been considered to have health-promoting potential. Recently, extensive laboratory research and epidemiologic studies have shown that many compounds present in tea show bioactivity and may be useful, for example, in treating a variety of illnesses and/or in producing enhanced physical or mental performance.

Polyphenolic compounds such as catechins and theaflavins have been shown to be particularly valuable. Some of the benefits of tea polyphenols may be directly linked to their antioxidant properties. The purported benefits include lowering blood lipid levels (e.g. cholesterol), anti-inflammation effects and anti-tumour effects.

Another tea compound which has been shown to have bioactivity is the amino acid theanine. For example, it is reported that theanine stimulates a-waves in the mammalian brain and bestows a relaxed but alert mental state to the individual.

Besides bioactive compounds, tea also contains compounds which are valued for their sensory qualities. In particular, tea has a unique aroma and is rich in aroma compounds.

Although some of the benefits of tea compounds may be apparent at consumption rates as low as a few cups per day, many individuals do not even achieve this modest consumption rate on a long term basis. Furthermore, tea beverages are less convenient to prepare than beverages prepared from non-tea-based beverage precursors, such as instant coffee, owing to the relatively slow rate of infusion of tea leaves and slow rate of dissolution of tea powders. Also, there is an increasing desire amongst consumers for products which deliver new sensory experiences but which products are derived from natural sources.

There have therefore been many previous efforts to provide products with enhanced levels of compounds derived from tea. In many cases the previous efforts have employed a process wherein the tea compounds are extracted from tea leaves using a solvent, such as water. For example, WO 2006/037511 (Unilever) discloses a process for preferentially extracting theanine from tea plant material which involves a short cold water extraction. One drawback with the known processes is that time and energy are employed to remove the large amounts of solvent required for exhaustive extraction.

Tea stem is a rich source of tea actives. WO 2006/021317 (Unilever) discloses a process comprising the steps of: (i) harvesting a source of tea plant material comprising stem and leaf material; (ii) physically separating the stem material from the leaf material to provide a tea plant source rich in stem; (iii) treating the stem source with at least one conventional tea processing unit operation selected from withering, maceration, grinding, steaming, fermentation, firing and infusing.

Thus we have recognised that there is a need to provide new materials enriched with tea compounds. We have also recognised that there is a need for a process for obtaining tea compounds from tea stem that does not require the use of large amounts of a solvent. We have found that such needs may be met by employing a process wherein juice is expressed from tea stem.

DEFINITIONS

Tea

"Tea" for the purposes of the present invention means material from *Camellia sinensis* var. *sinensis* and/or *Camellia sinensis* var. *assamica*.

"Stem" means the elongate tea plant material which is not part of the leaf proper.

"Leaf tea" for the purposes of this invention means a tea product that contains tea leaves and/or tea stem in an uninfused form, and that has been dried to a moisture content of less than 30% by weight, and usually has a water content in the range 1 to 10% by weight (i.e. "made tea").

"Green tea" refers to substantially unfermented tea. "Black tea" refers to substantially fermented tea. "Oolong tea" refers to partially fermented tea.

"Fermentation" refers to the oxidative and hydrolytic process that tea undergoes when certain endogenous enzymes and substrates are brought together, e.g., by mechanical disruption of the cells by maceration of the tea material. During this process colourless catechins in the material are converted to a complex mixture of yellow and orange to dark-brown polyphenolic substances.

"Fresh tea material" refers to tea stem and/or a mixture of tea leaves and stem, that has never been dried to a water content of less than 30% by weight, and usually has a water content in the range 60 to 90%.

"Tea compound" refers to any compound derived from tea material except for water. Thus tea compounds include all of the tea solids and tea volatiles.

Expressing Juice

As used herein the term "expressing juice" refers to squeezing out juice from fresh tea material using physical force, as opposed to extraction of tea solids with the use of a solvent. Thus the term "expressing" encompasses such means as squeezing, pressing, wringing, spinning and extruding. It is possible that a small amount of solvent (e.g. water) is added to the fresh tea material during the expression step. However, in order to prevent significant extraction of tea solids by the solvent, the moisture content of the leaves during expression is that of fresh tea material as defined hereinabove. In other words, during the expression step, the moisture content of the tea material is between 30 and 90% by weight, more preferably between 60 and 90%. It is also preferred that the fresh tea material is not contacted with non-aqueous solvent (e.g. alcohols) prior to or during expression, owing to the environmental & economic problems associated with such solvents.

Polyphenol

As used herein, the term "polyphenol" refers to one or more of a class compounds comprising a plurality of hydroxyl groups attached to one or more aromatic groups. Typical tea polyphenols include catechin, theaflavin and thearubigin.

As used herein the term "catechin" is used as a generic term for catechin, gallocatechin, catechin gallate, gallocatechin gallate, epicatechin, epigallocatechin, epicatechin gallate, epigallocatechin gallate, and mixtures thereof.

As used herein the term "theaflavin" is used as a generic term for theaflavin, isotheaflavin, neotheaflavin, theaflavin- 3-gallate, theaflavin-3'-gallate, theaflavin-3,3'-digallate, epitheaflavic acid, epitheaflavic acid-3'-gallate, theaflavic acid, theaflavic acid-3'-gallate and mixtures thereof. The structures of these compounds are well-known (see, for example, structures xi-xx in Chapter 17 of "Tea—Cultivation to consumption", K. C. Willson and M. N. Clifford (Eds), 1992, Chapman & Hall, London, pp. 555-601). The term theaflavins includes salt forms of these compounds. The preferred theaflavins are theaflavin, theaflavin-3-gallate, theaflavin-3'-gallate, theaflavin-3,3'-digallate and mixtures thereof, as these theaflavins are most abundant in tea.

Beverage

As used herein the term "beverage" refers to a substantially aqueous drinkable composition suitable for human consumption. The term "tea-based beverage" refers to a beverage comprising at least 0.01% by weight tea solids by weight of the beverage. Preferably the tea-based beverage comprises from 0.04 to 3% tea solids, more preferably from 0.06 to 2%, most preferably from 0.1 to 1%.

Enrichment and Purification

Where a given composition is said to be "enriched" in a tea compound, it is meant that the weight fraction of the tea compound in the mixture of tea compounds in the composition is at least one and a half times the weight fraction of the tea compound in the mixture of tea compounds in the tea juice immediately following expression. This can be expressed as shown in equation (1):

$$R(c_{TC}/c_{TOTAL})/(m_{TC}/m_{TOTAL}) \geq 1.5, \quad (1)$$

wherein R is the enrichment factor of a particular tea compound in a given composition, $c_{TC}$ is the mass of the particular tea compound in the given composition, $c_{TOTAL}$ is the total mass of tea compounds in the given composition, $m_{TC}$ is the mass of the particular tea compound in the tea juice and $m_{TOTAL}$ is the total mass of tea compounds in the tea juice.

Similarly "purification" refers to increasing the weight fraction of a tea compound in a composition.

SUMMARY OF THE INVENTION

We have found that juice can be readily expressed from tea stem and is rich in tea compounds whilst having a relatively low water content. Thus the juice provides an excellent source of tea compounds and requires less energy to dry than conventional tea extracts.

Therefore, in a first aspect, the present invention provides a process comprising the steps of:
a) providing fresh tea material rich in stem; and
b) expressing juice from the fresh tea material thereby to produce stem residue and tea juice comprising a mixture of tea compounds.

In a further aspect, the present invention provides tea juice obtained and/or obtainable by the process of the invention.

In a still further aspect, the present invention provides a beverage obtained and/or obtainable by diluting the tea juice.

DETAILED DESCRIPTION

Fresh Tea Material

Step (a) of the process comprises providing fresh tea material rich in stem.

The fresh tea material is preferably provided by a method comprising physically separating tea stem from tea leaves.

It is preferred that physical separation of leaves and stem occurs as a first step, however it is possible that the physical separation of leaf and stem takes place after withering or even after fermentation and/or steaming and/or roasting of the fresh tea material.

Separation may be achieved in a number of ways, for example by hand. However it is preferred that separation is carried out by a machine, such as that described in GB 893 551 (COLOMBO COMMERCIAL CO. Ltd). Such a machine may operate by threshing plucked fresh tea plant material and subsequently using blown air on a falling stream of thrashed material to provide two streams, one rich in stem and the other rich in leaves.

The physical separation step provides fresh tea material rich in stem, i.e. containing more stem than would be obtained merely by plucking fresh tea. Preferably the fresh tea material comprises at least 50% by weight of stem, more preferably at least 75% and most preferably from 90 to 100%.

Expression of Juice

Step (b) of the process of the invention comprises expressing juice from the fresh tea material thereby to produce stem residue and tea juice comprising a mixture of tea compounds.

If the amount of juice expressed is too low then it becomes difficult to separate the juice from the stem residue and/or leads to an inefficient process. Thus it is preferred that the amount of expressed juice is at least 10 ml per kg of the fresh tea material, more preferably at least 25 ml, more preferably still at least 50 ml and most preferably from 75 to 600 ml. When referring to the volume of juice expressed per unit mass of tea material it should be noted that the mass of the tea material is expressed on an "as is" basis and not a dry weight basis. Thus the mass includes any moisture in the material.

The expression step can be achieved in any convenient way so long as it allows for separation of the tea juice from the stem residue and results in the required quantity of juice. The machinery used to express the juice may, for example, include a hydraulic press, a pneumatic press, a screw press, a belt press, an extruder or a combination thereof.

The juice may be obtained from the fresh tea material in a single pressing or in multiple pressings of the material. Preferably the juice is obtained from a single pressing as this allows for a simple and rapid process.

In order to minimise degradation of the valuable tea compounds, it is preferred that the expression step is performed at ambient temperature. For example, the temperature of the tea material may be from 5 to 40° C., more preferably 10 to 30° C.

The time and pressure used in the expression step can be varied to yield the required amount of juice. Typically, however, the pressures applied to express the juice will range from 0.5 MPa (73 psi) to 10 MPa (1450 psi). The time over which the pressure is applied will typically range from 1 s to 1 hour, more preferably from 10 s to 20 minutes and most preferably from 30 s to 5 minutes.

Prior to expression, the fresh tea material may undergo a pre-treatment including, for example, a unit process selected from heat treatment to deactivate fermentation enzymes, maceration, withering, fermentation, freeze-thawing or a combination thereof.

If the tea juice and/or stem residue is to be used to obtain a green tea compound (e.g. catechin) it is preferred that the fresh material is heat treated to deactivate fermentation enzymes prior to expression. Suitable heat treatments include steaming and/or pan-frying.

If the tea juice and/or stem residue is to be used to obtain a black or oolong tea compound (e.g. theaflavin and/or thearubigin) it is preferred that the fresh material is not heat-treated to deactivate fermentation enzymes prior to expression. The fresh material may or may not be fermented prior to expression. If the fresh material is fermented prior to expression then it is particularly preferred that it is macerated prior to fermentation.

Whether or not the fresh material is fermented, maceration prior to expression may help in decreasing the time and/or pressure required to express the desired quantity of juice.

Processing the Juice

Tea juice separated from the stem residue is a valuable raw material for producing tea products and is a rich source of tea compounds.

The juice may be used to produce a green tea product, an oolong tea product or a black tea product. In the case of an oolong tea product or a black tea product then the juice is preferably expressed from at least partially fermented tea material in step (b) and/or the juice is subjected to a fermentation step after expression. In the case of a green tea product, the fresh material is not fermented before expression and the juice is not fermented after expression. It is possible that the juice is unfermented (e.g. by treating to deactivate the enzymes immediately following expression) whilst the stem residue is fermented to make black tea or oolong tea. Alternatively, the juice may be fermented following expression whilst the stem residue is heat treated to deactivate the fermentation enzymes and processed to a green tea.

Diluting to Make a Beverage

In one embodiment the tea juice is diluted to produce a beverage. A suitable process is described, for example, in CN 1 718 030 A (LANCANGJIANG BEER ENTPR GROUP).

The juice is preferably diluted with an aqueous medium, most preferably with water. The beverage typically comprises at least 85% water, more preferably at least 90%, optimally between 95 and 99.9% by weight of the beverage.

Because the juice is relatively rich in tea solids, it can be diluted many-fold whilst still imparting tea-qualities to the resulting beverage. Preferably, therefore, the juice is diluted by at least a factor of 2 to produce the beverage (i.e. 1 part of juice is combined with 1 part diluent by weight). More preferably the juice is diluted by a factor of at least 5 (i.e. 1 part of juice is combined with 4 parts diluent by weight) and most preferably by a factor of at least 7.

The juice can be used to make concentrated beverages with high levels of tea solids. For example, the juice may be diluted by a factor of less than 50, more preferably less than 25 and most preferably less than 15.

The mass of a single serve of the beverage may be, for example, less than 600 g, more preferably less than 350 g, more preferably still less than 250 g and most preferably from 20 to 150 g.

The pH of the beverage may, for example, be from 2.5 to 8, more preferably 3 to 6, most preferably from 3.5 to 6. The beverage may comprise a food grade acid and/or salt thereof such as citric, malic, ascorbic acid or a mixture thereof.

The beverage preferably comprises at least one nutrient selected from carbohydrate, protein, fat, vitamins, minerals and mixtures thereof. The beverage may be low calorie (e.g. have an energy content of less than 100 kCal per 100 g of the beverage) or may have a high calorie content (e.g. have an energy content of more than 100 kCal per 100 g of the beverage, preferably between 150 and 1000 kCal). It is most preferred that the beverage is very low calorie such that a single serving has a total energy content of less than 5 kCal, more preferably still less than 1 kCal.

The beverage may also comprise any of salt, sweetener, flavours, colours, preservatives, antioxidants or a mixture thereof.

The beverage is preferably packaged. The package will typically be a bottle, can, carton or pouch.

The beverage is preferably sanitised e.g. by pasteurisation or sterilisation.

Drying the Juice

In one embodiment the tea juice is dried to produce a concentrate such as a liquid concentrate or powder. Preferably the juice is dried to a moisture content of less than 80% by weight, more preferably less than 50% by weight, more preferably still less than 30% by weight and most preferably from 1 to 10% by weight. Any suitable drying process may be used including spray drying, freeze drying, oven drying, tray drying, vacuum drying or a combination thereof.

The concentrate or powder may, for example, be diluted or dissolved to produce a beverage, used as a food additive and/or used as a starting material for producing other tea-derived materials.

Combining the Juice with Leaf Tea

In one embodiment the tea juice is combined with leaf tea. For example the juice may be sprayed onto leaf tea. The juice may be diluted before combining with the leaf tea or may be mixed with the leaf tea in the form of a concentrate.

Fractionation of the Juice

In a particularly preferred embodiment, the process comprises (c) fractionating the mixture of tea compounds; and (d) recovering at least one fraction enriched in at least one tea compound.

The process may be used to purify any tea compound. However, the preferred tea compounds are those which show bioactivity and/or contribute to aroma. Thus it is preferred that the at least one tea compound is polyphenol, amino acid or an aroma compound.

If the at least one tea compound is polyphenol, then it may be, for example, catechin, theaflavin, thearubigin or a mixture thereof.

If the at least one tea compound is amino acid then it is preferably theanine.

If the at least one tea compound is an aroma compound then it will usually be volatile. By volatile is meant that it will have a vapour pressure of at least 1 Pa at 25° C. Preferably the aroma compound is methanol, acetaldehyde, dimethyl sulphide, 2-methyl-propanal, 2-methyl butanal, 3-methyl butanal, 1-penten-3-one, hexanal, 1-penten-3-ol, E-2-hexenal, Z-3-hexenyl acetate, Z-2-penten-1-ol, hexan-1-ol, Z-3-hexenol, E-2-hexenol, cis-linalool oxide, 1-octen-3-ol, trans-linalool oxide, linalool, α-terpinol, phenyl acetaldehyde, methyl salicylate, geraniol, benzyl alcohol, 2-phenylethanol or a mixture thereof.

Fractionation in step (c) can be achieved using any suitable process capable of separating tea compounds. Examples of such processes include the unit processes of membrane filtration, preparative chromatography, solvent extraction, precipitation, distillation and combinations thereof.

Membrane filtration may include microfiltration, ultrafiltration, nanofiltration, reverse osmosis or a combination thereof. The preferred filtration operation comprises ultrafiltration, nanofiltration or a combination thereof as these are especially effective at purifying bioactive compounds such as polyphenol and/or amino acid. Typically filtration will involve fractionating the mixture of tea compounds into at least one permeate fraction and at least one retentate fraction.

As used herein, the term "preparative chromatography" refers to a preparative process comprising the step of contacting the mixture of tea compounds with a chromatographic medium. The chromatographic medium is a substance which has a different affinity for at least 2 of the tea compounds in the mixture, examples include adsorbant materials. Typically the mixture will be fractionated by the preparative chromatography into at least two fractions differing in the degree to which they interact with the chromatographic medium. In a preferred embodiment, the preparative chromatography is column chromatography. Where the chromatography is column chromatography, the mixture will usually be eluted from the column and fractions collected at varying elution times.

Solvent extraction preferably comprises contacting the mixture of tea compounds with a solvent thereby to yield at least one soluble fraction and at least one insoluble fraction.

Precipitation usually comprises subjecting the mixture to a physical and/or chemical change such that soluble material precipitates out of solution and/or suspended material sediments or creams. Examples of chemical changes include changes in pH, solvent composition, concentration or a combination thereof. Examples of physical changes include heating or cooling, centrifugation or a combination thereof.

Distillation usually comprises heating the mixture to evaporate at least some volatile tea compounds. It is especially preferred that step (c) comprises distillation when the at least one tea compound is an aroma compound.

The at least one fraction enriched in at least one tea compound recovered on step (d) is preferably enriched in the tea compound such that the enrichment factor R is at least 1.7, more preferably at least 2 and most preferably from 3 to 1000.

In a preferred embodiment the at least one fraction is concentrated and/or dried. This allows for stable long-term storage of the fraction. Typically the fraction will be dried to less than 20% moisture by weight, more preferably less than 10% and optimally to 1 to 7% moisture.

Processing the Stem Residue

In order to maximise the efficiency of the process it is preferred that the stem residue is not discarded but is further processed to produce a commercially viable product. In a particularly preferred embodiment, the process comprises an additional step (e) wherein the stem residue is processed to produce made tea and/or is extracted with a solvent to produce a tea extract.

The stem residue may be processed to produce green tea, black tea or oolong tea. In the case of oolong tea and black tea step (e) comprises fermenting the stem residue.

Producing Made Tea

The manufacturing processes of green leaf tea, black leaf tea and oolong leaf tea are well known and suitable processes are described, for example, in "Tea: Cultivation to Consumption", K. C. Willson and M. N. Clifford (Eds), 1st Edn, 1992, Chapman & Hall (London), Chapters 13 and 14.

A step common to manufacture of all made teas is a drying step. In the case of oolong and black tea, the drying step usually also serves to deactivate the fermentation enzymes. Efficient drying requires high temperatures and so it is preferred that step (e) of the process comprises drying the stem residue at a temperature of at least 75° C., more preferably at least 90° C.

Producing Tea Extract

Although the stem residue may be extracted with the solvent prior to drying of the stem residue, in an especially preferred embodiment the extract is produced from made tea. Thus it is preferred that step (e) comprises processing the stem residue to produce made tea and then extracting the made tea with a solvent to produce a tea extract.

The most preferred solvent for use in step (e) is an aqueous solvent. Preferably the aqueous solvent comprises at least 50% water by weight of the solvent, more preferably at least 90% and most preferably from 99 to 100%.

The solvent may be cold and have a temperature, for example, in the range of from 1 to 50° C. It is most preferred, however, that the solvent is hot as hot solvents tend to be more efficient at extracting tea solids. Thus it is preferred that the solvent temperature in step (e) is greater than 50° C., more preferably at least 70° C. and most preferably from 80 to 100° C.

Preferably the solvent is contacted with the stem residue in step (e) for a time of at least 1 minute. However, because the stem residue usually has a good rate of infusion, it is preferred that the solvent is contacted with the residue in step (e) for a time of less than 1 hour, more preferably less than 30 minutes and most preferably less than 15 minutes.

The stem residue and solvent are preferably contacted in step (e) in a weight ratio in the range of 1:1 to 1:1000, more preferably from 1:4 to 1:100 and most preferably from 1:6 to 1:20.

Following contact of stem residue with solvent, the stem residue is usually separated from the liquid extract. Thus in a preferred embodiment, step (e) comprises de-leafing the extract. This de-leafing step can readily be achieved, for example, by filtering and/or centrifuging the extract.

In a most preferred embodiment, step (e) comprises removing at least some of the solvent from the extract to produce a concentrated tea extract. Where the solvent is aqueous this will involve drying the extract. The concentrated tea extract may be a liquid concentrate or a solid concentrate, such as a powder. Most preferred is that the tea extract is dried to a powder in step (e). Where the concentrated extract is a liquid, it will usually have a moisture content in the range of from 40 to 95% by weight. Where the concentrated extract is a solid concentrate it will typically have a moisture content of less than 30% by weight, more preferably from 1 to 10% by weight.

In a most preferred embodiment the tea extract is processed to produce an instant tea powder. Suitable processes include those described, for example, in Chapter 16 of "Tea: Cultivation to Consumption", K. C. Willson and M. N. Clifford (Eds), 1st Edn, 1992, Chapman & Hall (London).

Tea Juice Obtained by the Process

Tea juice separated from the stem residue is a valuable raw material for producing tea products and is a rich source of tea compounds.

The tea juice typically has a total soluble solids content of from 1 to 10% by weight, more preferably from 2 to 6% and most preferably from 3 to 5%.

The tea juice is particularly rich in amino acids such as theanine. The juice may, for example, comprise at least 4.0 mg theanine per ml of juice, more preferably at least 5.0 mg and most preferably from 6 to 10 mg. Alternatively or additionally, the juice may comprise at least 7% theanine by dry weight, more preferably at least 10% and most preferably from 12 to 20%.

The level of polyphenols in the juice is, however, relatively low. For example the juice may comprise less than 15 mg/ml total polyphenols, or even from 1 to 10 mg/ml total polyphenols. Alternatively or additionally, the juice may comprise less than 30% total polyphenols by dry weight, more preferably from 10 to 25%.

Additionally or alternatively, the tea juice may be characterised by the ratio of theanine to total polyphenols. Thus the tea juice (or a beverage obtained therefrom) will typically have a weight ratio of theanine to total polyphenols of at least 1:4, more preferably at least 1:3, more preferably still at least 1:2 and most preferably in the range 1:1.5 to 2:1.

In a further aspect the present invention provides a beverage comprising theanine and polyphenols and wherein the weight ratio of theanine to total polyphenols is at least 1:4, more preferably at least 1:3, more preferably still at least 1:2 and most preferably in the range 1:1.5 to 2:1. The beverage is preferably a tea-based beverage.

EXAMPLES

The present invention will be further described with reference to the following examples.

Example 1

This Example demonstrates the processing of fresh tea stem to produce stem juice.

Tea material (two leaves and a bud) was harvested and the leaves and buds then removed from the stem. The resulting stem material consisted of petiole and internode and was pressed (without steaming) using a hydraulic press (5 Tonnes applied to a 500 g mass of material inside a cylinder of diameter 160 mm, resulting in a downward pressure of 354 psi (2.44 MPa)) to express stem juice. The yield of stem juice was 20 ml/100 g stem. Table 1 shows a comparison of the stem juice with juice expressed as described above except that the leaves and buds were not separated from the stem.

The theanine content of the juice was determined by reversed phase HPLC chromatography using fluorimetric detection following post-column derivatisation with o-pthalaldehyde (as described in WO 2008/040627).

The total polyphenol content of the juice was determined using the Folin-Ciocalteu method as detailed in the International Standard published by the International Organization for Standardization as ISO 14502-1:2005(E).

TABLE 1

| Tea component | Amount by Total Volume of Juice (mg ml$^{-1}$) | | Amount by Dry Weight of Juice (%) | |
|---|---|---|---|---|
| | Stem Only | 2 Leaves + Bud | Stem Only | 2 Leaves + Bud |
| Total solids | 41.1 | 71.0 | 100.0 | 100.0 |
| Catechins | 1.8 | 18.7 | 4.4 | 26.3 |
| Theaflavins | 0.2 | 0.0 | 0.5 | 0.0 |
| Theanine | 6.5 | 3.6 | 15.8 | 5.1 |
| Caffeine | 1.4 | 4.0 | 3.4 | 5.6 |
| Total polyphenol | 8.7 | 24.8 | 21.2 | 34.9 |

It is apparent from the data in Table 1 that juice expressed from material rich in stem has a significantly higher level of theanine than juice expressed from material conventionally used for manufacturing tea products (i.e. two leaves and a bud). Furthermore tea juice has a high level of total solids compared with conventional aqueous tea extracts.

Example 2

This Example demonstrates the difference in theanine purity between juice expressed from stem and an aqueous extract of the stem.

Tea material (two leaves and a bud) was harvested and the stems were separated by hand from the leaf and bud. The stems were then coarsely cut with a vegetable cutter and then fermented for 2 hours.

The fermented stem was then spilt into two portions, portion A was immediately dried in a fluid bed dryer and used for aqueous extraction and portion B was pressed to express stem juice.

Dried tea stem from portion A was extracted with continuous stirring in 20° C. deionised water for 12 minutes (1 part tea:10 parts by weight water). The spent stem was separated from the cold extract using muslin cloth and then re-extracted with continuous stirring in 10 parts by weight of 90° C. deionised water for 12 minutes. The stems were separated from the hot extract using muslin cloth and discarded. The hot and cold extracts were combined, cooled to 20° C. and clarified using a Beckman Avanti J-25 centrifuge (JLA10.500 rotor, 10 minutes, 20° C.). The clarified extract had total solids of 2.3%.

500 g of portion B was pressed under 5 tonne pressure for 1 minute. Expressed juice was clarified using Beckman Avanti J-25 centrifuge (JLA10.500 rotor, 10 minutes, 20° C.). 96 g clarified juice was obtained with total solids of 3.6% by weight.

The theanine content of the juice and extract was determined by HPLC and is shown in Table 2.

TABLE 2

| Composition | Theanine concentration (mg ml$^{-1}$) | Theanine content in dry matter (wt %) |
|---|---|---|
| Stem Juice | 5.69 | 15.8 |
| Stem Extract | 2.57 | 11.2 |

It is apparent from the data in Table 2 that juice expressed from stem has theanine in a higher purity than that of stem extract.

The invention claimed is:

1. A process comprising the steps of:
   a) providing fresh tea material rich in stem; comprising at least about 50% by weight of stem;
   said fresh tea material never having been dried to a water content of less than 30% by weight and having a moisture content of about 30 to about 90% by weight of the fresh tea material;
   and followed by
   b) expressing juice from the fresh tea material thereby to produce stem residue and tea juice comprising a mixture of tea compounds; wherein during said expression step, the moisture content of the tea material is about 30 to about 90% by weight;
   wherein the tea juice comprises at least 4.0 mg theanine per ml of juice.

2. A process according to claim 1 comprising the additional step of drying the tea juice to a concentrate.

3. A process according to claim 1 wherein the tea juice is combined with leaf tea.

4. A process according to claim 1 comprising the additional steps of:
   c) fractionating the mixture of tea compounds; wherein said fractionation step comprises a unit process selected from membrane filtration, preparative chromatography, solvent extraction, precipitation, distillation and combinations thereof; and
   d) recovering at least one fraction enriched in at least one tea compound.

5. A process according to claim 4 wherein the at least one tea compound is amino acid.

6. A process according to claim 5 wherein the at least one tea compound is theanine.

7. A process comprising the steps of:
   a) providing fresh tea material rich in stem; comprising at least about 50% by weight of stem;
   said fresh tea material having a moisture content of about 30 to about 90% by weight of the fresh tea material;

followed by
b) expressing juice from the fresh tea material thereby to produce stem residue and tea juice comprising a mixture of tea compounds; wherein during said expression step, the moisture content of the tea material is about 30 to about 90% by weight;
   wherein the tea juice comprises at least 4.0 mg theanine per ml of juice; and
e) processing the stem residue to produce made tea and/or extracting the stem residue with a solvent to produce a tea extract.

8. The process according to claim 7 comprising the additional steps of:
   c) fractionating the mixture of tea compounds; wherein said fractionating step comprises a unit process selected from membrane filtration, preparative chromatography, solvent extraction, precipitation, distillation and combinations thereof; and
   d) recovering at least one fraction enriched in at least one tea compound.

* * * * *